United States Patent
Cai et al.

(10) Patent No.: US 12,000,814 B2
(45) Date of Patent: Jun. 4, 2024

(54) APPARATUS AND METHOD FOR PRODUCING POLICOSANOL HAVING SPECIFIC CHROMATOGRAPHIC FINGERPRINT

(71) Applicant: Institute of Biological Resources, Jiangxi Academy of Sciences, Nanchang (CN)

(72) Inventors: Lichuang Cai, Nanchang (CN); Jianping Liu, Nanchang (CN); Kexian Ouyang, Nanchang (CN); Xiongchang Guo, Nanchang (CN); Yue Tu, Nanchang (CN)

(73) Assignee: Institute of Biological Resources, Jiangxi Academy of Sciences, Nanchang (CN)

( * ) Notice: Subject to any disclaimer, the term of this patent is extended or adjusted under 35 U.S.C. 154(b) by 554 days.

(21) Appl. No.: 17/199,832

(22) Filed: Mar. 12, 2021

(65) Prior Publication Data

US 2021/0396724 A1  Dec. 23, 2021

(51) Int. Cl.
*B01D 3/10* (2006.01)
*C07C 29/84* (2006.01)
(Continued)

(52) U.S. Cl.
CPC ............ *G01N 30/88* (2013.01); *B01D 3/106* (2013.01); *C07C 29/84* (2013.01);
(Continued)

(58) Field of Classification Search
CPC ...... B01D 3/106; B01D 2202/00; C07C 29/84
See application file for complete search history.

(56) References Cited

U.S. PATENT DOCUMENTS

| 9,714,388 B1* | 7/2017 | Joshi ................ B01D 1/10 |
| 2011/0061224 A1* | 3/2011 | Ludwig ............. B01D 3/205 |
| | | 29/592.1 |

FOREIGN PATENT DOCUMENTS

| CN | 101402618 A | * | 4/2009 |
| CN | 201295543 Y | * | 8/2009 |

(Continued)

OTHER PUBLICATIONS

CN 101402618 A Espacenet Machine Translation Obtained Dec. 21, 2023. (Year: 2023).*

(Continued)

*Primary Examiner* — Jonathan Miller

(57) ABSTRACT

The present disclosure provides an apparatus and method for producing a policosanol having a specific chromatographic fingerprint. The apparatus of the present disclosure has a feed tank and receiving tanks which are connected to a vacuum system. The method of the present disclosure is carried out by a high vacuum rectification process and includes: firstly, feeding a saponified crude alkanol into a melting tank in which the material is melted and then flows into the feed tank, and then injecting the material into a rectifying still using a delivery pump, followed by first rectification under vacuum condition and sequential collection of fractions at different phases from the tower top and stillage residue from the tower bottom; and after the completion of the rectification of the first batch crude product, carrying out second feeding on the basis of consistent vacuum in the feed tank and the rectifying tower.

20 Claims, 1 Drawing Sheet

(51) Int. Cl.
  *G01N 30/88* (2006.01)
  *G01N 30/02* (2006.01)
(52) U.S. Cl.
  CPC .... *B01D 2202/00* (2013.01); *G01N 2030/025* (2013.01); *G01N 2030/884* (2013.01)

(56) References Cited

FOREIGN PATENT DOCUMENTS

CN      204051032 U    *  12/2014
CN      206027129 U    *  3/2017

OTHER PUBLICATIONS

CN 201295543 Y Espacenet Machine Translation Obtained Dec. 21, 2023. (Year: 2023).*
CN 206027129 U Espacenet Machine Translation Obtained Dec. 21, 2023. (Year: 2023).*
CN 204051032 U Innovation Q Machine Translation Obtained Dec. 21, 2023. (Year: 2023).*

* cited by examiner

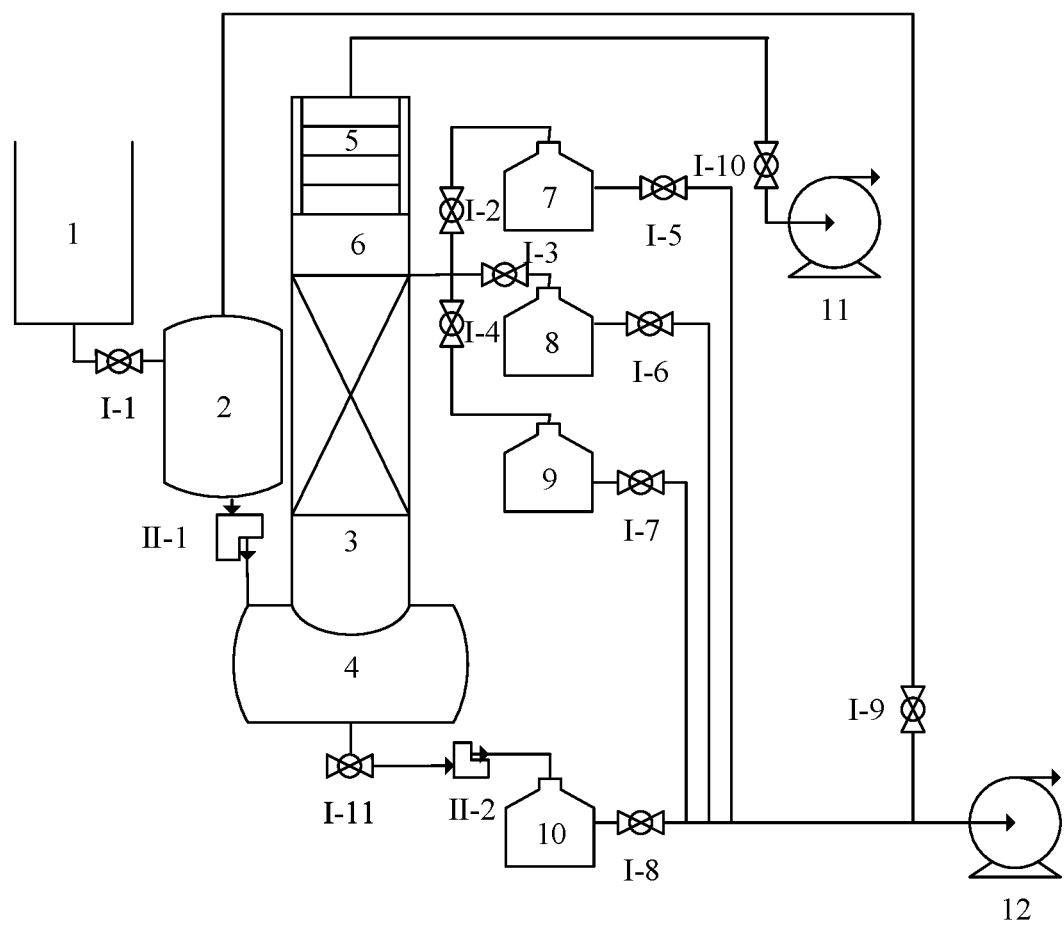

APPARATUS AND METHOD FOR PRODUCING POLICOSANOL HAVING SPECIFIC CHROMATOGRAPHIC FINGERPRINT

CROSS-REFERENCE TO RELATED APPLICATION

The present application claims priority to China Patent Application No. 202010581184.0 filed Jun. 23, 2020, the disclosure of which is hereby incorporated by reference in its entirety.

TECHNICAL FIELD

The present disclosure relates to the technical field of extraction, separation and deep processing of oils and fats, and in particular, to an apparatus and method for producing a policosanol having a specific chromatographic fingerprint.

BACKGROUND

Policosanol primarily comes from rice bran wax and beeswax and has major components including higher aliphatic alkanols such as docosanol, tetracosanol, hexacosanol, octacosanol, triacontanol and dotriacontanol. When the mass ratio of different components conforms to similar "traditional Chinese medicine fingerprint", the components can have the optimal synergistic effect and optimal physiological activities. Policosanol is mainly used in lipid-regulating drugs, health care products, high-end cosmetics, feed additives, etc.

At present, the policosanol is generally prepared from rice bran wax or beeswax by the processes of saponification, extraction (purification), filtration and so on. The purification process is critical for the chromatographic fingerprint of the policosanol and is currently carried out by recrystallization, molecular distillation and rectification.

The recrystallization needs to be carried out for many times, allowing the purity of octacosanol to be 60% at most. A large amount of solvent is needed during purification, and heavy metals would be brought in the solvent, thus resulting in residual solvent and heavy metals in the product. Moreover, the volatilization and emission of the solvent may have adverse effect on the environment, and the loss rate of the coarse product and the solvent reaches 10% during each recrystallization.

Molecular distillation is a distillation method carried out under high vacuum and a process for separating a liquid mixture based on the difference in evaporation rate between different components in the liquid mixture. The molecular distillation generally needs to be carried out more than once, after which the octacosanol having a purity of 60-90% can be obtained. The molecular distillation process has the advantages of simplicity, high raw material use ratio and no pollution to the environment over the recrystallization process. However, the molecular distillation is low in separation efficiency because no filler is used, i.e., there is only one tower plate. Moreover, the key point is that the proportions of different components of the product are uncontrollable and the policosanol having a specific "chromatographic fingerprint" cannot be produced with a failure to guarantee stable physiological activities.

Currently, the purification by the rectifying method is generally carried out by a high vacuum rectification process, and the rectification may be carried out twice or triple to provide the octacosanol having a purity of 40-95%. This method has the advantages of high separation efficiency and relatively controllable octacosanol content in the product at each phase over the distillation process. Nevertheless, this method has many disadvantages as follows: each feed and each discharge need to be carried out under normal pressure; the product needs to be collected at each phase after the vacuum degree and the tower top temperature are rebalanced; as a result, continuous batch feeding and discharging cannot be realized and the rectification time of each batch is prolonged. Moreover, every time normal pressure operation and negative pressure operation are switched, a great difference in octacosanol content of the product collected at the same phase in different times may be caused, and stable quality of the product cannot be guaranteed. Furthermore, twice or triple rectifications are needed, leading to not high enough production efficiency. Finally, the process can only produce a specific content of octacosanol and cannot produce the policosanol having the specific chromatographic fingerprint.

SUMMARY

In view of the above problems, the present disclosure provides an apparatus and method for producing a policosanol having a specific chromatographic fingerprint. When the policosanol is produced using the apparatus of the present disclosure, there is no need to switch normal pressure operation and negative pressure operation during feeding and discharging. In addition, feeding and discharging of continuous batches can be achieved while ensuring stable vacuum of a rectifying tower. The production efficiency is improved due to uninterrupted operation. Moreover, the product is stable in quality and the policosanol having the specific chromatographic fingerprint can be obtained.

To achieve the above objective, the present disclosure provides the following technical solutions.

An apparatus for producing a policosanol having a specific chromatographic fingerprint includes a melting tank 1;

a feed tank 2, with an inlet of the feed tank 2 being communicated with an outlet of the melting tank 1;

a rectifying tower 3 having a rectifying still 4 disposed at the bottom of the rectifying tower, a reflux condenser 5 disposed at the top of the rectifying tower, and a connection section 6 disposed between the top of the rectifying tower and the reflux condenser, with a discharge outlet being formed in the connection section 6, and a feed inlet being formed in the rectifying still 4 and communicated with an outlet of the feed tank 2;

a first receiving tank 7, a second receiving tank 8 and a third receiving tank 9 that are connected in parallel, with inlets of the first receiving tank 7, the second receiving tank 8 and the third receiving tank 9 being communicated with the discharge outlet of the connection section 6;

a fourth receiving tank 10 which is communicated with an outlet of the rectifying still 4;

a first vacuum unit 11 which is communicated with the reflux condenser 5; and a second vacuum unit 12 which is communicated with the first receiving tank 7, the second receiving tank 8, the third receiving tank 9, the fourth receiving tank 10 and the feed tank 2 separately.

Preferably, a first valve I-1 may be disposed on a pipe by which the outlet of the melting tank 1 is communicated with the inlet of the feed tank 2, and a second valve I-2, a third valve I-3 and a fourth valve I-4 may be disposed on pipes by which the discharge outlet of the connection section 6 is communicated with the inlets of the first receiving tank 7, the second receiving tank 8 and the third receiving tank 9, respectively.

A fifth valve I-5, a sixth valve I-6, a seventh valve I-7 and an eighth valve I-8 may be disposed on pipes by which the first receiving tank 7, the second receiving tank 8, the third receiving tank 9 and the fourth receiving tank 10 are communicated with the second vacuum unit 12, respectively.

A ninth valve I-9 may be disposed on a pipe by which the feed tank 2 is communicated with the second vacuum unit 12.

A tenth valve I-10 may be disposed on a pipe by which the reflux condenser 5 is communicated with the first vacuum unit 11.

A first delivery pump II-1 may be disposed on a pipe by which the outlet of the feed tank 2 is communicated with the feed inlet of the rectifying still 4.

An eleventh valve I-11 and a second delivery pump II-2 may be sequentially disposed on a pipe by which the outlet of the rectifying still 4 is communicated with an inlet of the fourth receiving tank 10 in a direction from the outlet of the rectifying still to the inlet of the fourth receiving tank.

Emptying valves may be mounted on the feed tank 2, the reflux condenser 5, the first receiving tank 7, the second receiving tank 8, the third receiving tank 9 and the fourth receiving tank 10; and an inflation inlet may be formed in the connection section 6.

Preferably, the rectifying tower 3 may be a packed tower which is 3-5 m high with 15-25 plates.

Preferably, the first vacuum unit 11 and the second vacuum unit 12 may be both four-stage roots vacuum units.

The present disclosure further provides a method for producing a policosanol having a specific chromatographic fingerprint using the apparatus according to the abovementioned solution, including the following steps:

step 1, feeding a saponified crude alkanol into the melting tank 1 in which the material is melted by heating and then flows into the feed tank 2, and injecting the material in the feed tank 2 into the rectifying still 4, followed by first rectification under vacuum condition and collection of fractions at different phases from the tower top by means of the first receiving tank 7, the second receiving tank 8 and the third receiving tank 9;

step 2, discharging the collected fractions and stillage residue after the completion of the first rectification, carrying out second feeding on the basis of consistent vacuum degree in the feed tank 2 and the rectifying tower 3, and starting receiving the fractions for the second time when the vacuum degree is consistent in the first receiving tank 7, the second receiving tank 8 and the third receiving tank 9 as well as the rectifying tower 3; and step 3, repeating step 2 to complete multiple times of rectifications, performing gas chromatographic detection on the collected fractions, and combining the product having similar chromatographic fingerprints in different times to obtain the policosanol having the specific chromatographic fingerprint;

where the policosanol having the specific chromatographic fingerprint includes the following components in percentage by mass: 0.1-15% of docosanol, 0.1-20% of tetracosanol, 0.5-30% of hexacosanol, 10.0-99.0% of octacosanol, 0.2-15% of triacontanol and 0.1-10% of dotriacontanol.

Preferably, the saponified crude alkanol may be a crude aliphatic alkanol prepared from rice bran wax or beeswax through a saponification reaction.

Preferably, the saponified crude alkanol may include the following components in percentage by mass: 0-7% of eicosanol, 0.1-10% of docosanol, 4-20% of tetracosanol, 1-14% of hexacosanol, 10-17% of octacosanol, 17-70% of triacontanol, 4-22% of dotriacontanol, 0.1-20% of tetratriacontanol, 0-14% of hexatriacontanol and 0-3% of octatriacontanol.

Preferably, the rectifying tower may operate at a vacuum degree of 20-50 Pa and a reflux ratio of 1:(5-20), and the rectifying still may be at a temperature of 230-250° C.

Preferably, collecting fractions at different phases may be specifically as follows: the range of a tower top temperature of 230-250° C. is divided into phases, each phase being 0.5-2° C., and the collected fractions are sequentially marked as first to nth fractions, n being an integer of less than or equal to 40; and the vacuum degree is consistent in the receiving tanks and the rectifying tower when the fractions are collected.

Preferably, collecting fractions at different phases may be specifically as follows: the first fraction is collected in the first receiving tank 7, while the second fraction is collected in the second receiving tank 8 and the third fraction is collected in the third receiving tank 9; when the third fraction is collected, the second valve I-2 and the third valve I-3 are closed to empty the first receiving tank 7 and the second receiving tank 8, followed by discharging the first fraction and the second fraction; the fifth valve I-5 and the sixth valve I-6 are opened; when the vacuum degree is consistent in the first receiving tank 7 and the second receiving tank 8 as well as the rectifying tower, the fifth valve I-5 and the sixth valve I-6 are closed, and the second valve I-2 and the third valve I-3 are orderly opened to receive the fourth fraction and the fifth fraction; when the fifth fraction is received, the fourth valve I-4 and the second valve I-2 are closed to empty the third receiving tank 9 and the first receiving tank 7, followed by discharging the third fraction and the fourth fraction; the seventh valve I-7 and the fifth valve I-5 are opened; when the vacuum degree is consistent in the third receiving tank 9 and the first receiving tank 7 as well as the rectifying tower, the seventh valve I-7 and the fifth valve I-5 are closed, and the fourth valve I-4 is opened to receive the sixth fraction; and the remaining fractions are received similarly until all the fractions are completely received.

The present disclosure provides an apparatus for producing a policosanol having a specific chromatographic fingerprint. A first vacuum unit and a second vacuum unit are arranged in the apparatus of the present disclosure, where the first vacuum unit is configured to control the vacuum degree in the rectifying tower and the second vacuum unit is configured control the vacuum degree in the receiving tank and the feed tank. The vacuum degree in the whole apparatus during feeding and discharging can be controlled conveniently using the two vacuum units. There is no need to switch normal pressure and negative pressure during feeding and discharging. In addition, feeding and discharging of continuous batches can be achieved while ensuring stable vacuum in the rectifying tower. The production efficiency is significantly improved due to uninterrupted operation. In addition, during traditional rectification operation, the tower top fractions are often directly withdrawn from the reflux condenser, while in the present disclosure, the fractions are withdrawn from the connection section which is disposed between the top of the rectifying tower and the reflux condenser; thus, the blockage of the pipe by the condensed liquid is avoided when the condensed liquid (which is a condensed liquid-solid mixture) is directly withdrawn from the reflux condenser. Furthermore, the apparatus of the present disclosure is provided with three fraction receiving tanks connected in parallel. The fractions at different phases are receiving using the three receiving tanks, so that the efficiency can be significantly improved.

The present disclosure further provides a method for producing a policosanol having a specific chromatographic fingerprint using the device according to the abovementioned solution. The method provided in the present disclosure is carried out by a high vacuum rectification process and includes: firstly, feeding a saponified crude alkanol into the melting tank in which the material is melted and then flows into the feed tank, and then injecting the material into the rectifying still, followed by first rectification under vacuum condition and sequential collection of fractions at different phases from the tower top and stillage residue from the tower bottom while keeping consistent vacuum degree in the receiving tanks and the rectifying tower during the collection of the fractions; and after the completion of the rectification of the first batch crude product, carrying out second feeding on the basis of consistent vacuum in the feed tank and the rectifying tower. The method provided in the present disclosure can obtain the policosanol including octacosanol of the desired purity by one rectification process and is more than 15 times higher than the molecular distillation method in separation efficiency. The method is simple in process and high in separation efficiency and is controllable in policosanol chromatographic fingerprint and stable in policosanol quality, thereby ensuring the activity of the policosanol. The method provided in the present disclosure does not need any solvent during production, thereby avoiding introduction of heavy metals and waste of raw materials, and is low in production cost, high in product purity, safe and environmentally friendly. Furthermore, according to the present disclosure, various policosanols in conformance with the chromatographic fingerprint as described in the present disclosure can be produced by controlling the temperature of the rectifying still and the reflux ratio.

BRIEF DESCRIPTION OF THE DRAWINGS

FIG. 1 is a structural schematic diagram of an apparatus for producing a policosanol having a specific chromatographic fingerprint, in which:

1 denotes a melting tank, while 2 a feed tank, 3 a rectifying tower, 4 a rectifying still, 5 a reflux condenser, 6 a connection section, 7 a first receiving tank, 8 a second receiving tank, 9 a third receiving tank, 10 a fourth receiving tank, 11 a first vacuum unit, 12 a second vacuum unit, I-1 a first valve, I-2 a second valve, I-3 a third valve, I-4 a fourth valve, I-5 a fifth valve, I-6 a sixth valve, I-7 a seventh valve, I-8 an eighth valve, I-9 a ninth valve, I-10 a tenth valve, I-11 an eleventh valve, II-1 a first delivery pump, and II-2 a second delivery pump.

DETAILED DESCRIPTION

The present disclosure provides an apparatus for producing a policosanol having a specific chromatographic fingerprint. The apparatus has a structure as shown in FIG. 1 and will be specifically described below with reference to FIG. 1.

The apparatus provided in the present disclosure includes a melting tank 1. The present disclosure has no special requirement for the melting tank and any melting tank well-known to those skilled in the art may be used.

The apparatus provided in the present disclosure includes a feed tank 2. An inlet of the feed tank is communicated with the melting tank and a first valve I-1 is preferably disposed on a communicating pipe therebetween.

The apparatus provided in the present disclosure includes a rectifying tower 3. In the present disclosure, the rectifying tower 3 is preferably a stacked tower. The stacked tower is preferably 3-5 m high, more preferably 4 m high, preferably with 15-25, more preferably 18-20 plates. In the present disclosure, the rectifying tower 3 has a rectifying still 4 disposed at the bottom of the tower and a reflux condenser 5 disposed at the top of the tower. A connection section 6 is disposed between the top of the rectifying tower and the reflux condenser. The connection section 6 is preferably 0.1-0.3 m long. A discharge outlet is formed in the connection section 6. Preferably, an inflation inlet is further formed in the connection section 6. In specific use, an inert gas is charged into the system via the inflation inlet to prevent explosion due to the combustion of the material. In the present disclosure, the condensed fraction is a liquid-solid mixture and may easily block the pipe when being withdrawn directly from the reflux condenser. The apparatus of the present disclosure is provided with a connection section for reflux of the condensed liquid in the reflux condenser. During reflux, part of the reflux liquid is withdrawn as the fraction from the discharge outlet of the connection section, while other part returns to the rectifying still, thereby avoiding the blockage of the pipe due to direct withdrawal of the fraction from the condenser. In the present disclosure, the reflux ratio can be controlled by controlling the volume ratio of the withdrawn fraction and the reflux liquid. In a specific embodiment of the present disclosure, the reflux ratio can be controlled by controlling the collection time. For example, when the reflux liquid is refluxed for 10 seconds and the fraction is collected for 1 second, the reflux ratio is 10:1.

In the present disclosure, a feed inlet is formed in the rectifying still 4. The feed inlet is communicated with the outlet of the feed tank 2 and a first delivery pump II-1 is preferably disposed on a communicating pipe therebetween.

The apparatus provided in the present disclosure includes a first receiving tank 7, a second receiving tank 8 and a third receiving tank 9 that are connected in parallel. The inlets of the first receiving tank 7, the second receiving tank 8 and the third receiving tank 9 are communicated with the discharge outlet of the connection section 6; and a second valve I-2, a third valve I-3 and a fourth valve I-4 are disposed on pipes by which the first receiving tank 7, the second receiving tank 8 and the third receiving tank 9 are communicated with the discharge outlet of the connection section 6, respectively.

The apparatus provided in the present disclosure includes a fourth receiving tank 10. In the present disclosure, the fourth receiving tank 10 is configured to receive stillage residue. The fourth receiving tank 10 is communicated with the outlet of the rectifying still 4 and an eleventh valve I-11 and a second delivery pump II-2 are preferably disposed in sequence on a communicating pipe therebetween in a direction from the outlet of the rectifying still to the inlet of the fourth receiving tank.

The apparatus provided in the present disclosure includes a first vacuum unit 11. In the present disclosure, the first vacuum unit 11 is communicated with the reflux condenser 5 and a tenth valve I-10 is preferably disposed on a communicating pipe therebetween. The first vacuum unit 11 is preferably a four-stage roots vacuum unit. The first vacuum unit 11 is configured to control the vacuum degree in the rectifying tower during rectification.

The apparatus provided in the present disclosure includes a second vacuum unit 12. In the present disclosure, the second vacuum unit 12 is preferably a four-stage roots vacuum unit. The second vacuum unit 12 is separately communicated with the first receiving tank 7, the second receiving tank 8, the third receiving tank 9, the fourth receiving tank 10 and the feed tank 2, and a fifth valve I-5, a sixth valve I-6, a seventh valve I-7 and an eighth valve I-8 are preferably disposed on pipes by which the first receiving tank 7, the second receiving tank 8, the third receiving tank 9 and the fourth receiving tank 10 are communicated with the second vacuum unit 12, respectively. A ninth valve I-9 is preferably disposed on a pipe by which the feed tank 2 is communicated with the second vacuum unit 12. The second unit is configured to control the vacuum degree in the receiving tanks and the feed tank, so that feeding of continuous batches is achieved while ensuring stable vacuum in the rectifying tower. In the present disclosure, the first receiving tank 7, the second receiving tank 8 and the third receiving tank 9 are configured to receive fractions and can be used alternately under the control of valves, so that continuous discharging can be achieved without stop. The fourth receiving tank is configured to receive stillage residue.

In the present disclosure, emptying valves are mounted on the feed tank 2, the connection section 6, the first receiving tank 7, the second receiving tank 8, the third receiving tank 9 and the fourth receiving tank 10. The specific mounting method for the emptying valves is not specifically defined in the present disclosure and any method well-known to those skilled in the art may be used.

The present disclosure further provides a method for producing a policosanol having a specific chromatographic fingerprint using an apparatus according to the abovementioned solution, including the following steps:

step 1, feed a saponified crude alkanol into the melting tank 1 in which the material is melted by heating and then flows into the feed tank 2, and inject the material in the feed tank 2 into the rectifying still 4, followed by first rectification under vacuum condition and collection of fractions at different phases from the tower top by means of the first receiving tank 7, the second receiving tank 8 and the third receiving tank 9;

step 2, discharge the collected fractions and stillage residue after the completion of the first rectification, carry out second feeding on the basis of consistent vacuum degree in the feed tank 2 and the rectifying tower 3, and start receiving the fractions for the second time when the vacuum degree is consistent in the first receiving tank 7, the second receiving tank 8 and the third receiving tank 9 as well as the rectifying tower 3; and step 3, repeat step 2 to complete multiple times of rectifications, perform gas chromatographic detection on the collected fractions, and combine the product having similar chromatographic fingerprints in different times to obtain the policosanol having the specific chromatographic fingerprint.

According to the present disclosure, the saponified crude alkanol is fed into the melting tank 1 in which the material is melted by heating and then flows into the feed tank 2, and the material in the feed tank 2 is injected into the rectifying still 4, followed by first rectification under vacuum condition and collection of fractions at different phases from the tower top by means of the first receiving tank 7, the second receiving tank 8 and the third receiving tank 9. In the present disclosure, the saponified crude alkanol is preferably a crude aliphatic alkanol prepared from rice bran wax or beeswax through a saponification reaction. The saponified crude alkanol includes the following components in percentage by mass: 0-7% of eicosanol, 0.1-10% of docosanol, 4-20% of tetracosanol, 1-14% of hexacosanol, 10-17% of octacosanol, 17-70% of triacontanol, 4-22% of dotriacontanol, 0.1-20% of tetratriacontanol, 0-14% of hexatriacontanol and 0-3% of octatriacontanol, preferably 0-3% of eicosanol, 1-8% of docosanol, 5-15% of tetracosanol, 2-13% of hexacosanol, 13-15% of octacosanol, 25-50% of triacontanol, 5-20% of dotriacontanol, 0.5-18% of tetratriacontanol, and 1-4% of hexatriacontanol, In the present disclosure, the temperature of heating to melt the material preferably ranges from 80 to 90° C. The material which is melted by heating flows into the feed tank 2 and the material in the feed tank 2 is preferably injected into the rectifying still 4 by means of the first delivery pump I-1. After entering the rectifying still 4, the material is subjected to first rectification under vacuum condition in a rectification system composed of the rectifying tower 3, the rectifying still 4 and the reflux condenser 5. During rectification, the vacuum degree in the rectifying tower 3 is preferably 20-50 Pa; the reflux ratio is preferably 1:(5-20), more preferably 1:(10-15); and the temperature of the rectifying still preferably ranges from 230 to 250° C. During rectification, an inert gas (in particular, nitrogen) is preferably charged into the system via the inflation inlet of the connection section 6 to prevent explosion due to the combustion of the material. According to the present disclosure, policosanols having different chromatographic fingerprints can be preferably produced by controlling the temperature of the rectifying still and the reflux ratio. In the present disclosure, the product having a higher content of heavy components may be collected from the tower top at a higher temperature of the rectifying still.

In the present disclosure, collecting fractions at different phases is specifically as follows: the range of a tower top temperature of 230-250° C. is divided into phases, each phase being 0.5-2° C., and the collected fractions are sequentially marked as first to nth fractions, n being an integer of less than or equal to 40, preferably 18-30, further preferably 18-25; and the vacuum degree is consistent in the receiving tanks and the rectifying tower when the fractions are collected.

In the present disclosure, collecting fractions at different phases is more specifically as follows: the first fraction is collected in the first receiving tank 7, while the second fraction is collected in the second receiving tank 8 and the third fraction is collected in the third receiving tank 9; when the third fraction is collected, the second valve I-2 and the third valve I-3 are closed to empty the first receiving tank 7 and the second receiving tank 8, followed by discharging the first fraction and the second fraction; the fifth valve I-5 and the sixth valve I-6 are opened; when the vacuum degree is consistent in the first receiving tank 7 and the second receiving tank 8 as well as the rectifying tower, the fifth valve I-5 and the sixth valve I-6 are closed, and the second valve I-2 and the third valve I-3 are orderly opened to receive the fourth fraction and the fifth fraction; when the fifth fraction is received, the fourth valve I-4 and the second valve I-2 are closed to empty the third receiving tank 9 and the first receiving tank 7, followed by discharging the third fraction and the fourth fraction; the seventh valve I-7 and the fifth valve I-5 are opened; when the vacuum degree is consistent in the third receiving tank 9 and the first receiving tank 7 as well as the rectifying tower, the seventh valve I-7 and the fifth valve I-5 are closed, and the fourth valve I-4 is opened to receive the sixth fraction; and the remaining fractions are received similarly until all the fractions are completely received.

According to the present disclosure, the collected fractions and stillage residue are discharged after the completion of the first rectification. The stillage residue is preferably discharged into the fourth receiving tank 10 by means of the eleventh valve I-11 and the second delivery pump II-2. Specifically, the eighth valve I-8 is opened first and then closed when the vacuum degree is consistent in the fourth receiving tank and the rectifying tower, and the eleventh valve I-11 is opened to discharge the stillage residue into the fourth receiving tank by means of the second delivery pump II-2. The eleventh valve I-11 is closed to empty the fourth receiving tank, followed by discharging the stillage residue. In the present disclosure, the method for discharging the fractions is consistent with that in the abovementioned solution, which will not be described redundantly here. In the present disclosure, the rectification is completed until no fraction flows out of the tower top.

According to the present disclosure, after the fractions and the stillage residue are discharged, the second feeding is carried out on the basis of consistent vacuum degree in the feed tank 2 and the rectifying tower 3. The reception of the fractions for the second time is started when the vacuum degree is consistent in the first receiving tank (7), the second receiving tank (8) and the third receiving tank (9) as well as the rectifying tower (3). The vacuum degree in the feed tank is preferably controlled by the ninth valve I-9 in the present disclosure. The method for receiving the fractions for the second time is consistent with the method for receiving the fractions of the first batch, which will not be described redundantly here.

According to the present disclosure, step 2 is repeated to complete multiple times of rectifications, followed by performing gas chromatographic detection on the collected fractions and combining the product having similar chromatographic fingerprints in different times to obtain the policosanol having the specific chromatographic fingerprint. In the present disclosure, there is no special requirement for the gas chromatographic detection method and any method well-known to those skilled in the art may be used. In a specific embodiment, the composition of fractions at different phases is preferably detected by gas chromatography and the fractions having similar chromatographic fingerprints at different phases in different times are combined. Then, the combined fractions are mixed in a mixing ratio according to the target chromatographic fingerprint of the policosanol to obtain the policosanol having the target chromatographic fingerprint, where the specific mixing ratio may be determined according to the components of the combined fractions and the components of the policosanol having the target chromatographic fingerprint. In a specific embodiment of the present disclosure, different combined fractions may further be subjected to secondary rectification, thereby obtaining different high purity higher aliphatic alkanols by separation. The rectification method is consistent with that in the abovementioned solution, which will not be described redundantly here.

In the present disclosure, the policosanol having the specific chromatographic fingerprint includes the following components in percentage by mass: 0.1-15% of docosanol, 0.1-20% of tetracosanol, 0.5-30% of hexacosanol, 10.0-99.0% of octacosanol, 0.2-15% of triacontanol and 0.1-10% of dotriacontanol, preferably 0.5-12% of docosanol, 0.5-18% of tetracosanol, 1-28% of hexacosanol, 15-95% of octacosanol, 0.5-12% of triacontanol and 0.5-9% of dotriacontanol, The technical solutions in the present disclosure will be described clearly and completely below in conjunction with examples in the present disclosure.

The compositions of fractions in the examples were measured by gas chromatography, and the specific method may refer to the Journal (CAI, Li-chuang et al., Study on New Extraction Technique of Higher Aliphatic Alkanols from Beeswax, Institute of Biological Resources, Jiangxi Academy of Sciences, 2011, 29(4): 473-476).

Example 1

(1) A certain amount of saponified crude alkanol (its chromatographic fingerprint includes 0.1-0.3% of docosanol, 4-14% of tetracosanol, 5-14% of hexacosanol, 11-17% of octacosanol, 17-23% of triacontanol, 10-20% of dotriacontanol, 12-20% of tetratriacontanol, 10-14% of hexatriacontanol and 1-3% of octatriacontanol) from rice bran wax was fed into the melting tank 1 in which the material was melted by heating and then flowed into the feed tank 2, and then 18 kg of material was accurately injected into the rectifying still 4 using the first delivery pump II-1, followed by first rectification with a vacuum degree of 20-50 Pa, a temperature of the rectifying still ranging from 230 to 250° C. and a reflux ratio of 1:(5-20). After the rectification, 18 fractions within a temperature range of 210-230° C. were sequentially collected from the tower top (the collected fractions were sequentially marked as P101-P118). P101 was collected in the first receiving tank 7, while P102 is collected in the second receiving tank 8 and P103 is collected in the third receiving tank 9. When P103 was collected, the second valve I-2 and the third valve I-3 were closed to empty the first receiving tank 7 and the second receiving tank 8, followed by discharging P101 and P102. The fifth valve I-5 and the sixth valve I-6 were opened. When the vacuum degree was consistent in the first receiving tank 7 and the second receiving tank 8 as well as the rectifying tower, the fifth valve I-5 and the sixth valve I-6 were closed, and the second valve I-2 and the third valve I-3 were orderly opened to receive P104 and P105. When P105 was received, the fourth valve I-4 and the second valve I-2 were closed to empty the third receiving tank 9 and the first receiving tank 7, followed by discharging the third fraction and the fourth fraction. The seventh valve I-7 and the fifth valve I-5 were opened. When the vacuum degree was consistent in the third receiving tank 9 and the first receiving tank 7 as well as the rectifying tower, the seventh valve I-7 and the fifth valve I-5 were closed, and the fourth valve I-4 was opened to receive P106. The remaining fractions were received similarly until all the fractions are completely received.

(2) The stillage residue (marked as P119) was discharged after the completion of the rectification of the first batch crude product. When the vacuum degree in the feed tank was regulated to be consistent with that of the system, second feeding was carried out. The mentioned operation was repeated to complete the rectifications of 10 batches.

Gas chromatographic detection was performed on the collected fractions and the content of each component in the fractions of different batches and the stillage residue was analyzed, with the results being listed in table 1.

TABLE 1

Contents of Components in Fractions P101-P118
of Different Batches and Stillage Residue P119

| Phase | C22 | C24 | C26 | C28 | C30 | C32 | C34 | C36 | C38 |
|---|---|---|---|---|---|---|---|---|---|
| P101 | 80-90% | 10-20% | 0.1-1% | — | — | — | — | — | — |
| P102 | — | 70-90% | 10-30% | 0.1-1% | — | — | — | — | — |
| P103 | — | 40-60% | 30-50% | 1-20% | — | — | — | — | — |
| P104 | — | 15-40% | 20-40% | 20-40% | — | — | — | — | — |
| P105 | — | 1-15% | 20-40% | 40-60% | — | — | — | — | — |
| P106 | — | 0.1-1% | 10-30% | 60-80% | — | — | — | — | — |
| P107 | — | — | 1-10% | 80-99% | 0.1-10% | — | — | — | — |
| P108 | — | — | 1-10% | 60-80% | 1-20% | — | — | — | — |
| P109 | — | — | 0.1-1% | 40-60% | 30-50% | — | — | — | — |
| P110 | — | — | — | 20-45% | 50-70% | 0.1-1% | — | — | — |
| P111 | — | — | — | 10-30% | 60-80% | 1-30% | — | — | — |
| P112 | — | — | — | 1-15% | 35-55% | 30-40% | — | — | — |
| P113 | — | — | — | 0.1-5% | 25-40% | 40-60% | — | — | — |
| P114 | — | — | — | — | 20-30% | 60-80% | 0.1-10% | — | — |
| P115 | — | — | — | — | 10-20% | 30-50% | 10-40% | — | — |
| P116 | — | — | — | — | 0.1-10% | 10-30% | 40-60% | 0.1-1% | — |
| P117 | — | — | — | — | — | 1-10% | 60-85% | 5-30% | — |
| P118 | — | — | — | — | — | — | 30-50% | 40-60% | 1-10% |
| P119 | — | — | — | — | — | — | 25-35% | 30-40% | 20-30% |

The meaning of the percentage by mass in table 1 was explained by taking the content of C22 in P101 for example: the rectifications of 10 batches were carried out to obtain 10 P101 fractions, and P101 in each batch was detected, where the lowest content of C22 was 80% and the highest content was 90%, and then the content of C22 in P101 was expressed as 80-90% in table 1.

(3) The fractions having similar chromatographic fingerprints of gas chromatography were combined according to the detection results. Different combined fractions could also be subjected to secondary rectification, thereby obtaining different high purity higher aliphatic alkanols by separation. Two or more fractions were mixed in a particular mass ratio, thereby obtaining the policosanol having the target chromatographic fingerprint. For example, P101, P106 and P112 were mixed in a mass ratio of 10:65:25, thereby obtaining the policosanol in conformance with the mentioned target chromatographic fingerprint.

Example 2

As in example 1, with the difference that the saponified crude alkanol from the rice bran wax was replaced by a saponified crude alkanol from beeswax (including 0.5-7% of eicosanol, 2-10% of docosanol, 10-20% of tetracosanol, 1-14% of hexacosanol, 10-15% of octacosanol, 35-70% of triacontanol, 4-22% of dotriacontanol and 0.1-1% of tetratriacontanol). The rectifications of 10 batches were carried out. Gas chromatographic detection was performed on the collected fractions and the content of each component in the fractions of different batches and the stillage residue was analyzed, with the results being listed in table 2.

TABLE 2

Contents of Components in Fractions P101-P118
of Different Batches and Stillage Residue P119

| Phase | C20 | C22 | C24 | C26 | C28 | C30 | C32 | C34 |
|---|---|---|---|---|---|---|---|---|
| P101 | 60-90% | 10-20% | 0.1-1% | — | — | — | — | — |
| P102 | 0.1-1% | 70-90% | 1-15% | 0.1-1% | — | — | — | — |
| P103 | — | 40-60% | 20-35% | 0.5-15% | 0.1-1% | — | — | — |
| P104 | — | 25-45% | 30-50% | 20-35% | 1-15% | — | — | — |
| P105 | — | 10-30% | 45-60% | 30-40% | 10-30% | — | — | — |
| P106 | — | 5-15% | 20-40% | 20-30% | 25-45% | — | — | — |
| P107 | — | 1-10% | 10-25% | 10-20% | 40-60% | — | — | — |
| P108 | — | 0.1-5% | 1-15% | 5-15% | 55-75% | — | — | — |
| P109 | — | — | 0.1-1% | 1-10% | 70-90% | 0.1-1% | — | — |
| P110 | — | — | — | 0.5-5% | 90-99% | 0.1-5% | — | — |
| P111 | — | — | — | 0.1-1% | 75-90% | 5-20% | 0.1-1% | — |
| P112 | — | — | — | — | 55-75% | 20-40% | 0.1-1% | — |
| P113 | — | — | — | — | 25-60% | 35-60% | 1-5% | — |
| P114 | — | — | — | — | 10-30% | 55-80% | 1-5% | — |
| P115 | — | — | — | — | 1-10% | 75-95% | 5-15% | — |
| P116 | — | — | — | — | 0.1-1% | 30-60% | 15-20% | 0.1-1% |
| P117 | — | — | — | — | — | 1-10% | 25-60% | 1-25% |
| P118 | — | — | — | — | — | 0.1-1% | 60-80% | 20-40% |
| P119 | — | — | — | — | — | — | 50-60% | 40-50% |

The meaning of each percentage by mass in table 2 was the same as that in table 1.

(3) The fractions having similar chromatographic fingerprints of gas chromatography were combined according to the detection results. Different combined fractions could also be subjected to secondary rectification, thereby obtaining different high purity higher aliphatic alkanols by separation. Two or more fractions were mixed in a particular mass ratio, thereby obtaining the policosanol having the target chromatographic fingerprint. For example, P103 and P111 were mixed in a mass ratio of 1:3, thereby obtaining the policosanol in conformance with the mentioned target chromatographic fingerprint.

The foregoing are merely descriptions of preferred embodiments of the present disclosure. It should be noted that a person of ordinary skill in the art may further make several improvements and modifications without departing from the principle of the present disclosure, and such improvements and modifications should be deemed as falling within the protection scope of the present disclosure.

What is claimed is:

1. An apparatus for producing a policosanol having a specific chromatographic fingerprint, comprising: a melting tank (1);
    a feed tank (2), with an inlet of the feed tank (2) being communicated with an outlet of the melting tank (1);
    a rectifying tower (3) having a rectifying still (4) disposed at a bottom of the rectifying tower, a reflux condenser (5) disposed at a top of the rectifying tower, and a connection section (6) disposed between the top of the rectifying tower and the reflux condenser, with a discharge outlet being formed in the connection section (6), and a feed inlet being formed in the rectifying still (4) and communicated with an outlet of the feed tank (2); wherein an inflation inlet is formed in the connection section (6) to charge an inert gas into a system during a rectifying process;
    a first receiving tank (7), a second receiving tank (8) and a third receiving tank (9) that are connected in parallel, with inlets of the first receiving tank (7), the second receiving tank (8) and the third receiving tank (9) being communicated with the discharge outlet of the connection section (6);
    a fourth receiving tank (10) which is communicated with an outlet of the rectifying still (4);
    a first vacuum unit (11) which is communicated with the reflux condenser (5); and
    a second vacuum unit (12) which is communicated with the first receiving tank (7), the second receiving tank (8), the third receiving tank (9), the fourth receiving tank (10) and the feed tank (2) separately, to control vacuum degrees in the first receiving tank (7), the second receiving tank (8), the third receiving tank (9), the fourth receiving tank (10), and the feed tank (2).

2. The apparatus according to claim 1, wherein a first valve (I-1) is disposed on a pipe by which the outlet of the melting tank (1) is communicated with the inlet of the feed tank (2), and a second valve (I-2), a third valve (I-3) and a fourth valve (I-4) are disposed on pipes by which the discharge outlet of the connection section (6) is communicated with the inlets of the first receiving tank (7), the second receiving tank (8) and the third receiving tank (9), respectively;
    a fifth valve (I-5), a sixth valve (I-6), a seventh valve (I-7) and an eighth valve (I-8) are disposed on pipes by which the first receiving tank (7), the second receiving tank (8), the third receiving tank (9) and the fourth receiving tank (10) are communicated with the second vacuum unit (12), respectively;
    a ninth valve (I-9) is disposed on a pipe by which the feed tank (2) is communicated with the second vacuum unit (12);
    a tenth valve (I-10) is disposed on a pipe by which the reflux condenser (5) is communicated with the first vacuum unit (11);
    a first delivery pump (II-1) is disposed on a pipe by which the outlet of the feed tank (2) is communicated with the feed inlet of the rectifying still (4);
    an eleventh valve (I-11) and a second delivery pump (II-2) are sequentially disposed on a pipe by which the outlet of the rectifying still (4) is communicated with an inlet of the fourth receiving tank (10) in a direction from the outlet of the rectifying still to the inlet of the fourth receiving tank;
    emptying valves are mounted on the feed tank (2), the reflux condenser (5), the first receiving tank (7), the second receiving tank (8), the third receiving tank (9) and the fourth receiving tank (10).

3. The apparatus according to claim 1, wherein the rectifying tower (3) is a packed tower which is 3-5 m high with 15-25 plates.

4. The apparatus according to claim 2, wherein the rectifying tower (3) is a packed tower which is 3-5 m high with 15-25 plates.

5. The apparatus according to claim 1, wherein the first vacuum unit (11) and the second vacuum unit (12) are both four-stage roots vacuum units.

6. The apparatus according to claim 2, wherein the first vacuum unit (11) and the second vacuum unit (12) are both four-stage roots vacuum units.

7. A method for producing a policosanol having a specific chromatographic fingerprint using an apparatus according to claim 1, comprising following steps:
    step 1, feeding a saponified crude alkanol into the melting tank (1) in which the material is melted by heating and then flows into the feed tank (2), and injecting the material in the feed tank (2) into the rectifying still (4), followed by first rectification under vacuum condition and collection of fractions at different phases from the tower top by means of the first receiving tank (7), the second receiving tank (8) and the third receiving tank (9);
    step 2, discharging the collected fractions and stillage residue after the completion of the first rectification, carrying out second feeding on the basis of consistent vacuum degree in the feed tank (2) and the rectifying tower (3), and starting receiving the fractions for the second time when the vacuum degree is consistent in the first receiving tank (7), the second receiving tank (8) and the third receiving tank (9) as well the rectifying tower (3); and
    step 3, repeating step 2 to complete multiple times of rectifications, performing gas chromatographic detection on the collected fractions, and combining the product having similar chromatographic fingerprints in different times to obtain the policosanol having the specific chromatographic fingerprint; wherein the policosanol having the specific chromatographic fingerprint comprises the following components in percentage by mass: 0.1-15% of docosanol, 0.1-20% of tetracosanol, 0.5-30% of hexacosanol, 10.0-99.0% of octacosanol, 0.2-15% of triacontanol and 0.1-10% of dotriacontanol.

8. The method for producing a policosanol having a specific chromatographic fingerprint according to claim 7, wherein a first valve (I-1) is disposed on a pipe by which the outlet of the melting tank (1) is communicated with the inlet of the feed tank (2), and a second valve (I-2), a third valve (I-3) and a fourth valve (I-4) are disposed on pipes by which the discharge outlet of the connection section (6) is communicated with the inlets of the first receiving tank (7), the second receiving tank (8) and the third receiving tank (9), respectively;

a fifth valve (I-5), a sixth valve (I-6), a seventh valve (I-7) and an eighth valve (I-8) are disposed on pipes by which the first receiving tank (7), the second receiving tank (8), the third receiving tank (9) and the fourth receiving tank (10) are communicated with the second vacuum unit (12), respectively;

a ninth valve (I-9) is disposed on a pipe by which the feed tank (2) is communicated with the second vacuum unit (12);

a tenth valve (I-10) is disposed on a pipe by which the reflux condenser (5) is communicated with the first vacuum unit (11);

a first delivery pump (II-1) is disposed on a pipe by which the outlet of the feed tank (2) is communicated with the feed inlet of the rectifying still (4);

an eleventh valve (I-11) and a second delivery pump (II-2) are sequentially disposed on a pipe by which the outlet of the rectifying still (4) is communicated with an inlet of the fourth receiving tank (10) in a direction from the outlet of the rectifying still to the inlet of the fourth receiving tank;

emptying valves are mounted on the feed tank (2), the reflux condenser (5), the first receiving tank (7), the second receiving tank (8), the third receiving tank (9) and the fourth receiving tank (10).

9. The method for producing a policosanol having a specific chromatographic fingerprint according to claim 7, wherein the rectifying tower (3) is a packed tower which is 3-5 m high with 15-25 plates.

10. The method for producing a policosanol having a specific chromatographic fingerprint according to claim 8, wherein the rectifying tower (3) is a packed tower which is 3-5 m high with 15-25 plates.

11. The method for producing a policosanol having a specific chromatographic fingerprint according to claim 7, wherein the first vacuum unit (11) and the second vacuum unit (12) are both four-stage roots vacuum units.

12. The method for producing a policosanol having a specific chromatographic fingerprint according to claim 8, wherein the first vacuum unit (11) and the second vacuum unit (12) are both four-stage roots vacuum units.

13. The method according to claim 7, wherein the saponified crude alkanol is a crude aliphatic alkanol prepared from rice bran wax or beeswax through a saponification reaction.

14. The method according to claim 8, wherein the saponified crude alkanol is a crude aliphatic alkanol prepared from rice bran wax or beeswax through a saponification reaction.

15. The method according to claim 7, wherein the saponified crude alkanol comprises the following components in percentage by mass: 0-7% of eicosanol, 0.1-10% of docosanol, 4-20% of tetracosanol, 1-14% of hexacosanol, 10-17% of octacosanol, 17-70% of triacontanol, 4-22% of dotriacontanol, 0.1-20% of tetratriacontanol, 0-14% of hexatriacontanol and 0-3% of octatriacontanol.

16. The method according to claim 13, wherein the saponified crude alkanol comprises the following components in percentage by mass: 0-7% of eicosanol, 0.1-10% of docosanol, 4-20% of tetracosanol, 1-14% of hexacosanol, 10-17% of octacosanol, 17-70% of triacontanol, 4-22% of dotriacontanol, 0.1-20% of tetratriacontanol, 0-14% of hexatriacontanol and 0-3% of octatriacontanol.

17. The method according to claim 14, wherein the saponified crude alkanol comprises the following components in percentage by mass: 0-7% of eicosanol, 0.1-10% of docosanol, 4-20% of tetracosanol, 1-14% of hexacosanol, 10-17% of octacosanol, 17-70% of triacontanol, 4-22% of dotriacontanol, 0.1-20% of tetratriacontanol, 0-14% of hexatriacontanol and 0-3% of octatriacontanol.

18. The method according to claim 7, wherein the rectifying tower operates at a vacuum degree of 20-50 Pa and a reflux ratio of 1:(5-20), and the rectifying still is at a temperature of 230-250° C.

19. The method according to claim 7, wherein collecting fractions at different phases is specifically as follows: the range of a tower top temperature of 230-250° C. is divided into phases, each phase being 0.5-2° C., and the collected fractions are sequentially marked as first to nth fractions, n being an integer of less than or equal to 40; and the vacuum degree is consistent in the receiving tanks and the rectifying tower when the fractions are collected.

20. The method according to claim 19, wherein collecting fractions at different phases is specifically as follows: the first fraction is collected in the first receiving tank (7), while a second fraction is collected in the second receiving tank (8) and a third fraction is collected in the third receiving tank (9); when the third fraction is collected, the second valve (I-2) and the third valve (I-3) are closed to empty the first receiving tank (7) and the second receiving tank (8), followed by discharging the first fraction and the second fraction; the fifth valve (I-5) and the sixth valve (I-6) are opened; when the vacuum degree is consistent in the first receiving tank (7) and the second receiving tank (8) as well as the rectifying tower, the fifth valve (I-5) and the sixth valve (I-6) are closed, and the second valve (I-2) and the third valve (I-3) are orderly opened to receive a fourth fraction and a fifth fraction; when the fifth fraction is received, the fourth valve (I-4) and the second valve (I-2) are closed to empty the third receiving tank (9) and the first receiving tank (7), followed by discharging the third fraction and the fourth fraction; the seventh valve (I-7) and the fifth valve (I-5) are opened; when the vacuum degree is consistent in the third receiving tank (9) and the first receiving tank (7) as well as the rectifying tower, the seventh valve (I-7) and the fifth valve (I-5) are closed, and the fourth valve (I-4) is opened to receive a sixth fraction; and remaining fractions are received similarly until all the fractions are completely received.

* * * * *